Figure 1:
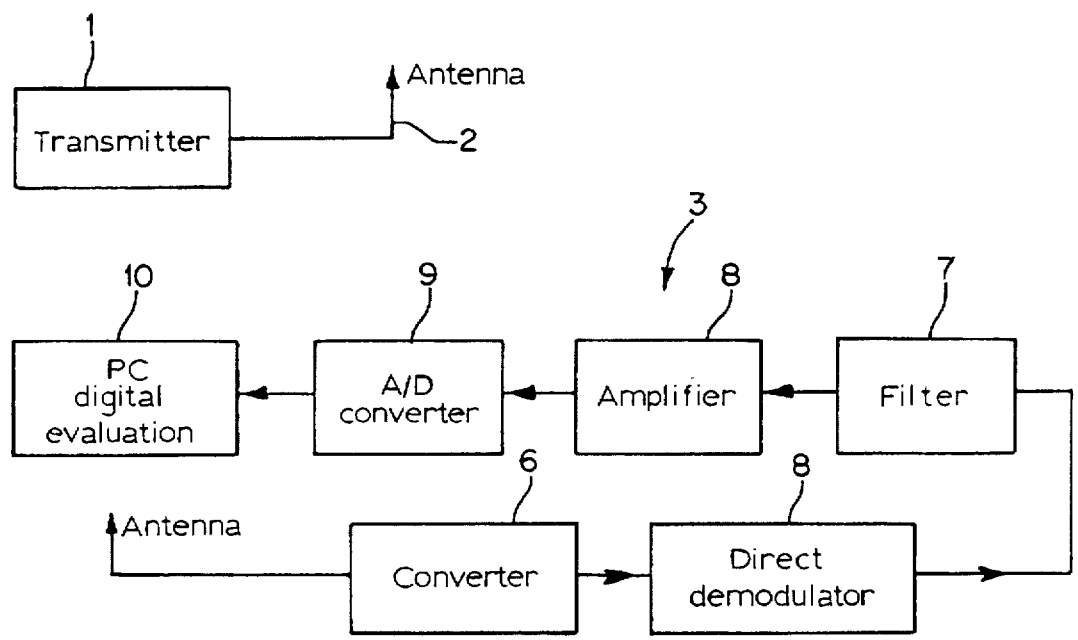

United States Patent [19]

Schmidt

[11] Patent Number: 5,790,032

[45] Date of Patent: Aug. 4, 1998

[54] METHOD OF AND APPARATUS FOR DETECTING LIVING BODIES

[75] Inventor: Gerd Juergen Schmidt, Frankfurt am Main, Germany

[73] Assignee: Selectronic Gesellschaft fur Scherheitstechnik und Sonderelektronik mbH, Werden/Havel, Germany

[21] Appl. No.: 676,322

[22] PCT Filed: Jan. 20, 1995

[86] PCT No.: PCT/DE95/00062

§ 371 Date: Sep. 8, 1996

§ 102(e) Date: Sep. 8, 1996

[87] PCT Pub. No.: WO95/20170

PCT Pub. Date: Jul. 27, 1995

[30] Foreign Application Priority Data

Jan. 20, 1994 [DE] Germany ............ 94 00 950 U

[51] Int. Cl.[6] .................................. G08B 23/00
[52] U.S. Cl. ............... 340/573; 349/539; 364/148; 364/724.01; 364/724.12; 128/653.1; 128/660; 128/670.1; 128/671; 342/28; 329/301; 329/305; 329/313

[58] Field of Search .................. 340/573, 539; 364/148, 724.01, 724.12, 724.17, 728.03, 724.19; 342/27, 28; 128/653.1, 668, 670, 671; 375/324, 327; 329/301, 305, 313

[56] References Cited

U.S. PATENT DOCUMENTS

| 3,780,725 | 12/1973 | Goldberg | 128/662.04 |
|---|---|---|---|
| 4,559,499 | 12/1985 | Bursztejn et al. | 329/309 |
| 5,122,765 | 6/1992 | Pataut | 332/105 |
| 5,438,625 | 8/1995 | Klippel | 381/96 |
| 5,448,501 | 9/1995 | Hablov | 128/653.1 |
| 5,573,012 | 11/1996 | McEwan | 128/782 |
| 5,623,402 | 4/1997 | Johnson | 364/162 |
| 5,627,899 | 5/1997 | Craven et al. | 381/98 |

Primary Examiner—Jeffery A. Hofsass
Assistant Examiner—Benjamin C. Lee

[57] ABSTRACT

An apparatus detects living bodies, in particular human living bodies, by electromagnetic signals. The apparatus has a receiver device for electromagnetic signals that includes a device for obtaining frequency components that are characteristic in respect to living bodies, out of the magnetic signals. The receiver device includes a direct demodulator.

25 Claims, 14 Drawing Sheets

Frequency: 1.221481  Value: 5276.754

METHOD OF AND APPARATUS FOR DETECTING LIVING BODIES

DESCRIPTION

The invention concerns an apparatus according to the classifying portion of claim 1, a method according to the classifying portion of claim 3 and uses of the method and/or the apparatus.

In the description hereinafter the detection of living bodies, in particular human living bodies, is used to denote detecting the presence of bodies in the living condition. Such detection is important for example when searching for persons buried alive as a result of natural catastrophes or in the case of accidents if there is neither visual nor audible contact with the buried persons. As the survival period is limited, great importance is attributed to immediately detecting whether there are still living persons buried alive, and rescuing such persons after they have been located. The term 'locating' is used in the description hereinafter to denote establishing the place where the living body is disposed.

The previously used methods and apparatuses for detecting or locating persons buried alive are generally not capable of distinguishing persons who are buried alive, who are still living, from dead persons.

The use of search dogs is possible only to a limited degree in respect of time, experience has shown that an animal working with a high level of concentration, after two to three hours, requires a lengthy recovery period which results in the search being interrupted. In addition, as it is the sense of smell which is the main consideration in regard to animals, they are not capable of only searching for persons who are still living, and for that reason valuable time is often lost in rescuing dead persons, and that time is then no longer available for rescuing people who are still alive.

Listening devices for picking up signs of life or knocking fail to operate in relation to unconscious people. In addition, error-free location is frequently not possible due to reflection of sound in the debris.

In order to achieve improved location after avalanche accidents, it is known to carry transmitter devices on the body, which permit location to be effected after the person has been buried alive, on the basis of the emitted electromagnetic radiation. However devices of that kind do not make it possible to arrive at any conclusion about the life functions of the wearer and are generally not available in the case of accidents or when people are buried alive as a result of natural catastrophes.

There is therefore a need for improved equipment and methods of detecting living bodies, in particular human living bodies, in order to be able to proceed more quickly and in a more targeted fashion by qualified rescue of people who are still alive.

The object of the invention is so to develop an apparatus according to the classifying portion of claim 1 and a method according to the classifying portion of claim 14 that, while avoiding the above-described disadvantages, the desired improved rescue options are afforded.

That object is attained by an apparatus having the features of claim 1 and a method having the features of claim 13.

Further advantageous configurations and uses of the method and the apparatus are set forth in the appendant claims.

The inventors found that living bodies and therefore also human living bodies generally surprisingly influence high-frequency electromagnetic signals, even over relatively long distances, by virtue of their heartbeat and their respiration activity. As heartbeat and in most cases also respiration activity occur in unconscious people, those functions can be considered as an indication of the existence of life, for the purposes of the present invention.

As those life functions generally take place within known frequency ranges which with the human heart rate can be from about 0.5 through 3.4 Hz and are normally about 1 through 2 Hz, and in the case of respiration can extend between 0.1 and 1.5 Hz, that defines characteristic frequency ranges which are clearly different from those of other living creatures such as for example the search dogs which are frequently used on site.

A frequency range of 0.01 to 10 Hz always appears to include frequencies which are of interest in regard to the life functions of a body.

It was possible to show that human living bodies through which electromagnetic radiation passes impress on such radiation a detectable phase modulation effect at the above-described frequencies. In the case of monofrequency radiation that therefore involves side bands of the electromagnetic carrier signal, which are substantially displaced by the foregoing frequencies relative to the base frequency emitted.

What was surprising was the realisation that even without emitted transmission power, just the receiver device together with the device for obtaining the frequency components which are characteristic of living bodies was in a position to provide the desired identification effect.

That means that the presence of a living body, at least in the vicinity of the receiver device, already results in detectable signal components in the above-mentioned frequency ranges, without in that respect the need for through-radiation with a carrier signal to be effected.

Furthermore it is possible to provide information about the number of located persons, on the basis of received and also processed signals. In that respect, use is made of the principle of biological variety and specificity, on the basis of which the heart and respiration frequency patterns of different people differ. As from a number of people of four however, it is generally no longer possible clearly to arrive at a distinction by virtue of frequency superimposition of the respective frequencies. As from that number of people, it is then only possible to provide the information that: 'there are at least four people present'.

With the receiver device for electromagnetic signals and the device for obtaining frequency components which are characteristic in respect of living bodies, without additional emitted signals, the inventors were already in a position of reliably detecting living bodies at up to more than 3 metres distance or approximately the distance of the storey of a building.

In the simplest embodiment of the invention the direct demodulator described hereinafter, in the form of a diode direct receiver for receiving the frequency components which are characteristic in respect of living bodies, was already sufficient.

In addition transmitters were later used, with which through-radiation of the detection area was effected, and reflected, transmitted or scattered radiation was received, the investigation thereof for pronounced frequency components providing the proof of the presence of living bodies.

So that electromagnetic radiation can still be received through dense debris, even at some distance, frequencies of the electromagnetic radiation of some hundred megahertz to about 10 gigahertz were used, which ensured a high depth of penetration.

That radiation experienced phase modulation which added side bands displaced by some Hertz to the high-frequency carrier signal. With conventional reception procedures, detection of frequency bands which are so close together would have required short term-stable oscillators with deviations of less than $10^{-12}$, which hitherto was considered to be unattainable at reasonable cost. That problem is made more acute by the low levels of received signal powers.

Some of the advantages of the embodiments described in the appendant claims are discussed hereinafter.

The transition from detection to location is made possible by a receiving antenna with a defined directional characteristic which, for optimum adaptation to the spatial search area, has secondary or side lobes which are as small as possible, a large forward lobe and a rearward lobe which is as small as possible.

The use of known phase modulators initially appears obvious. Homodyne, heterodyne and PLL (Phase Locked Loop) methods and the excitation of the flank of a local oscillation circuit are known. It has been found however that none of the foregoing processes was capable of supplying the desired results at an expenditure that was reasonable for portable use and which was cost-viable for stationary use. It was only the use of a direct demodulator which permits direct separation of the modulation frequency from the modulated frequency, that lead to the desired results. It is assumed however that, with suitable apparatus expenditure and improved circuit arrangements, the foregoing methods can be used in accordance with the present invention.

With a component with a non-linear current/voltage characteristic as the frequency-selective element, it was possible to provide for demodulation of the frequency components which are of interest. A diode, a bipolar or a field effect transistor could be successfully used as the element with a non-linear characteristic.

Those components are both inexpensively obtainable and also non-critical in regard to their use. The optimum working range of those components of from about 100 kHz to 200 MHz could be used at higher reception frequencies by means of a frequency conversion device connected upstream of the demodulator. Although that frequency conversion device added tolerable distortion in the time area to the signal, it did however superimpose only a slight amount of additional noise.

The signal to be received could be raised with a transmitter device for transmitting an electromagnetic carrier signal at a fixed frequency; however a very high level of attention had to be paid to the stability of the carrier frequency in order to exclude undesirable modulation effects in the frequency range which is of interest. A simple quartz-stabilised analog transmission circuit with an oscillator circuit of high quality surprisingly showed itself to be a suitable oscillator, after an adequate transient or build-up time.

When using a transmission antenna with a fixed directional characteristic, a kind of cross-bearing effect is achieved, together with the receiving antenna, and location is possible not only in a direction in space but in defined three-dimensional areas in space.

That location effect can be successfully used in relation to homogeneous debris or in a free environment. In that way, the method and the apparatus according to the invention can also be used for object monitoring and/or safeguarding. The specific embodiments show, at a later point in this description, both a portable and a static monitoring arrangement.

The use of an analog sampling filter, unlike high-frequency digital filters, did not exhibit any detrimental additional frequency components and crucially contributed to the quality of the signal obtained. Additional undesirable signal components such as for example noise and superimposed interference were prevented by limiting the band width of the electromagnetic signal prior to the sampling operation and prior to A/D-conversion to high frequencies.

The use of an analog high pass filter for preventing low-frequency components in respect of the frequency-dependent 1/f-noise of the transmission oscillator and internal structural units was also important.

The unexpectedly good operation of the apparatus according to the invention and the method according to the invention also permits use thereof in other areas.

People who are in danger of committing suicide can be monitored in psychiatry or in places of detention, without requiring constant inspection by personnel who are in charge of such people.

Figure 2:
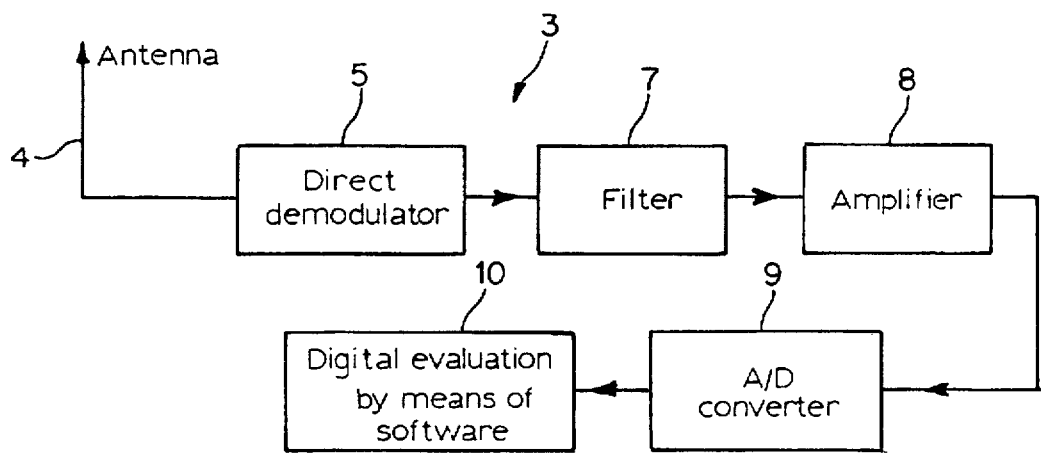
Figure 3:
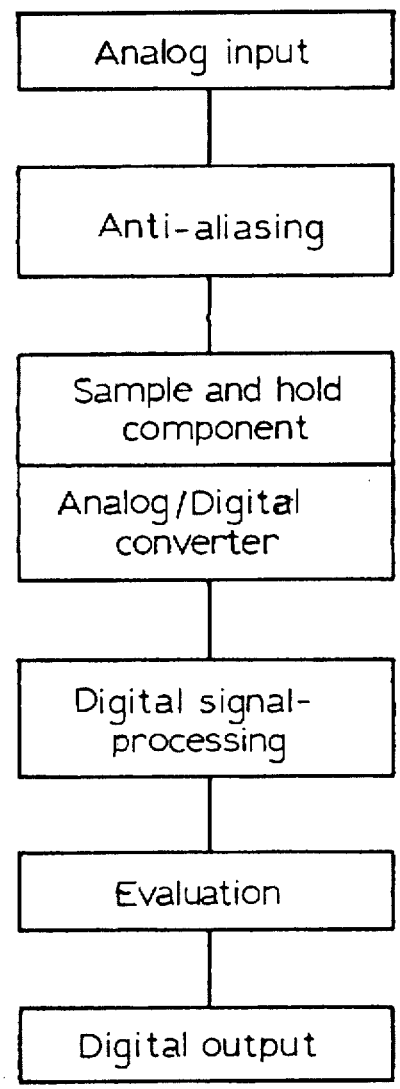
Figure 4:
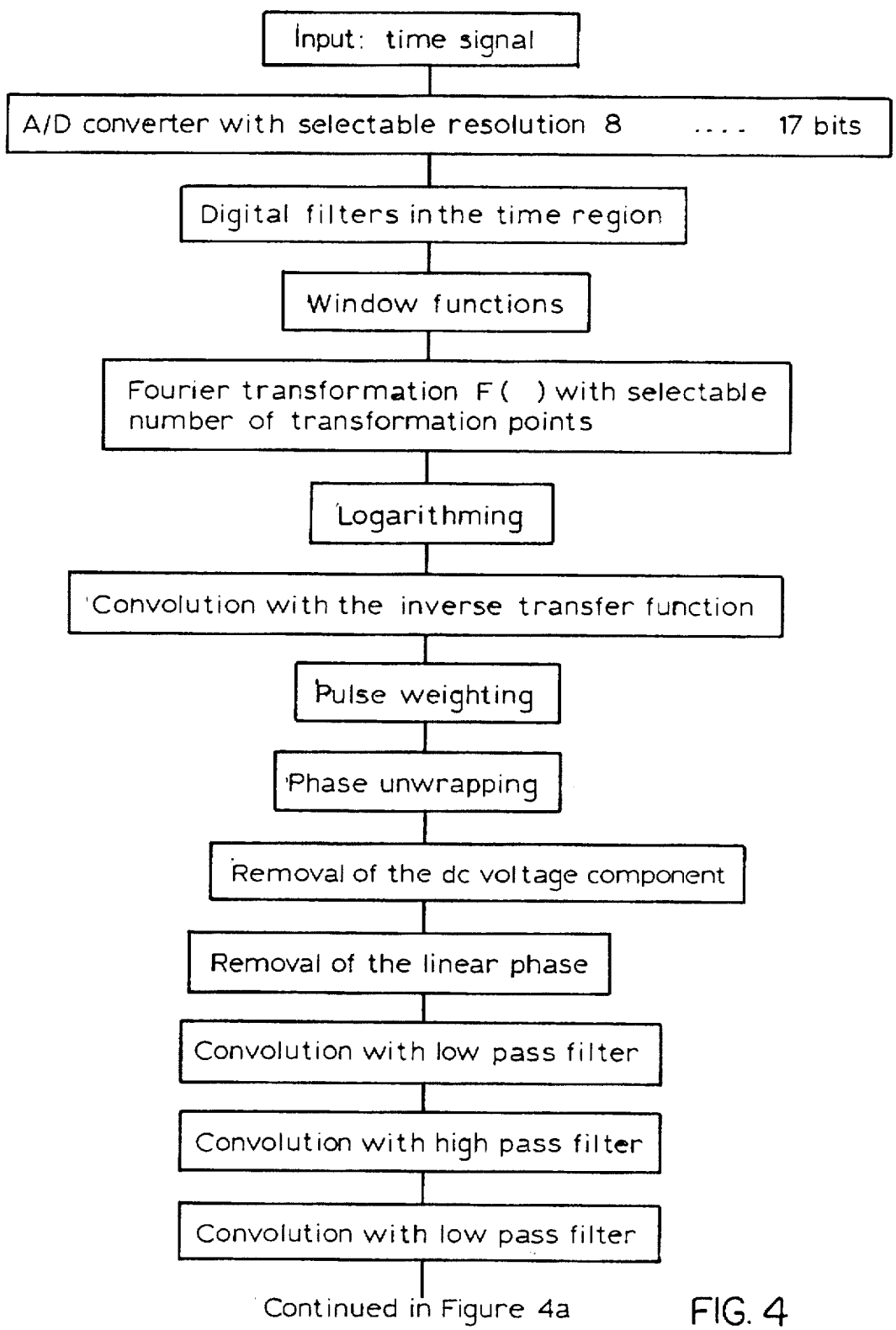
Figure 4A:
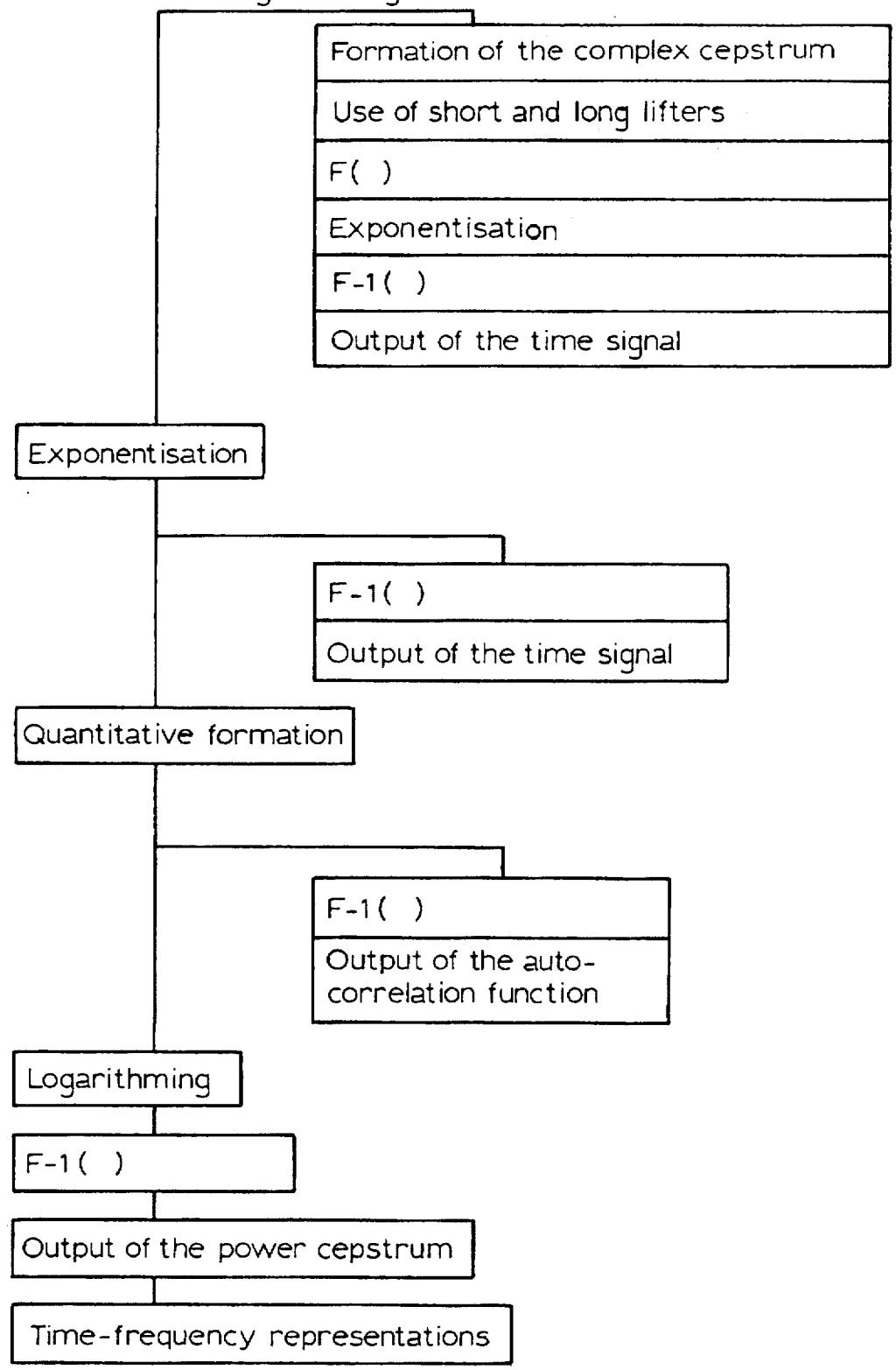
Figure 5:
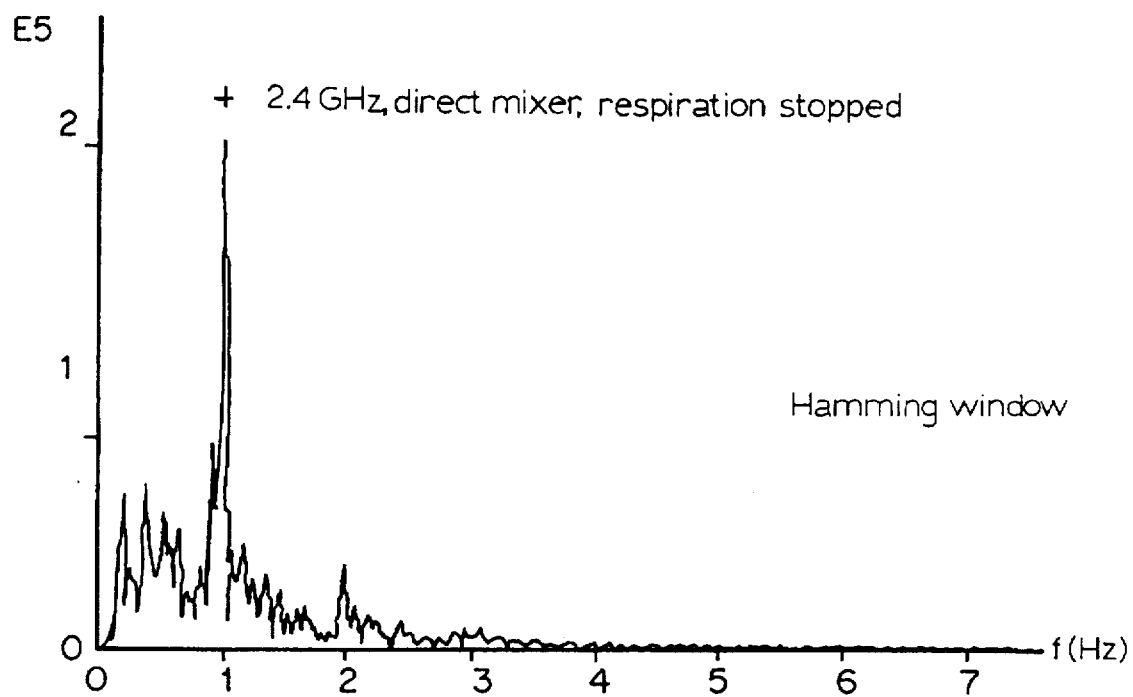
Figure 6:
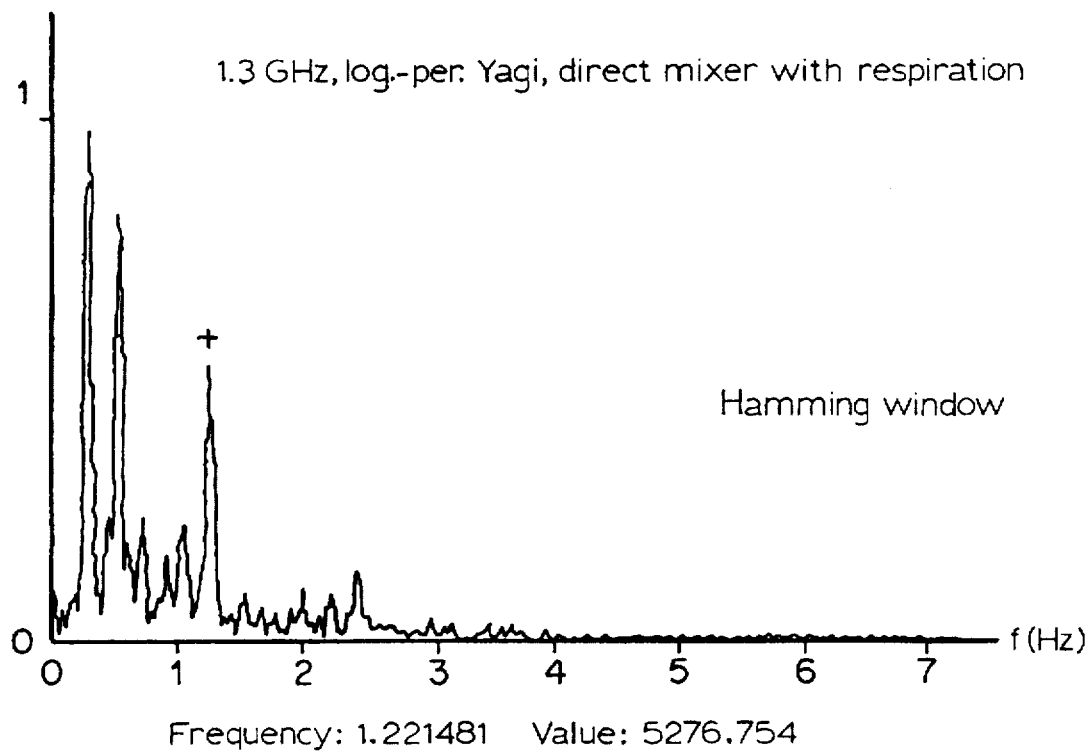
Figure 8A:
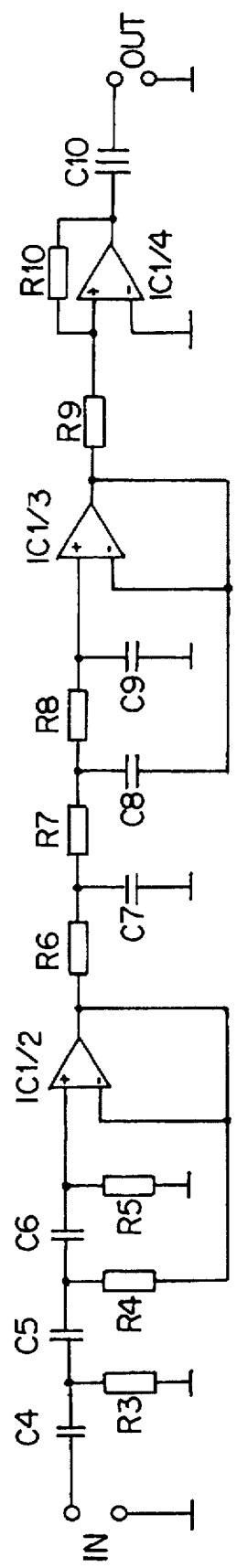
Figure 8B:
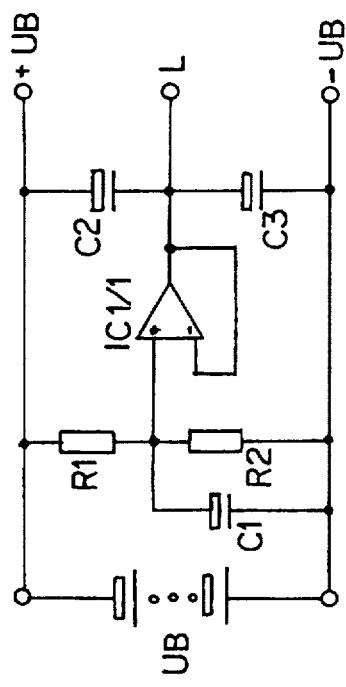
Figure 7:
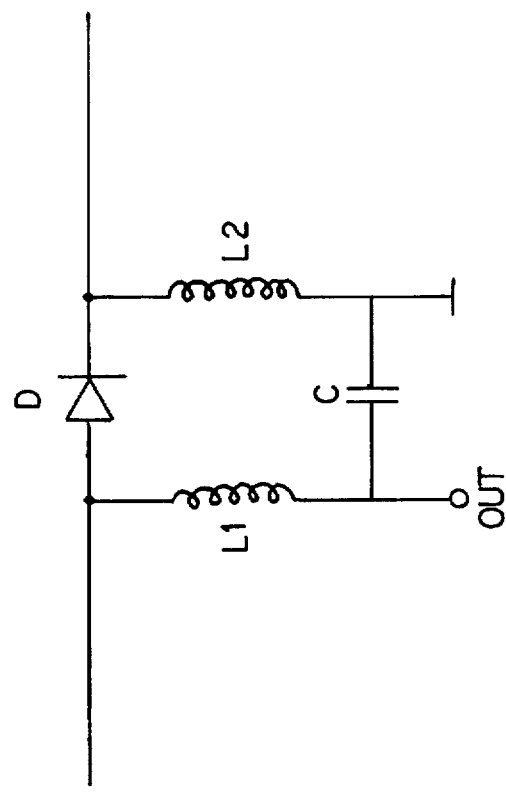
Figure 9:
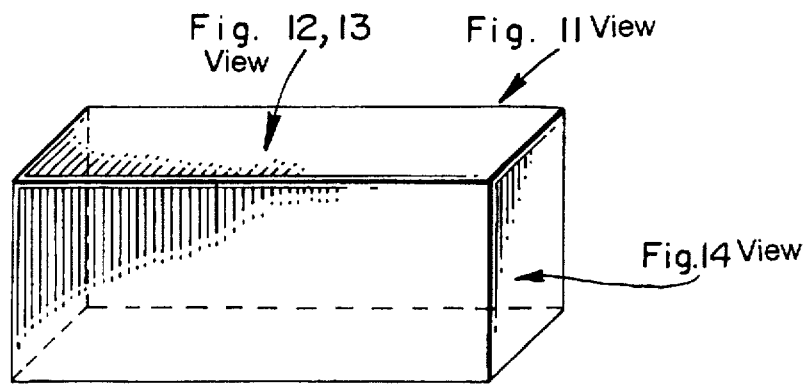
Figure 10:
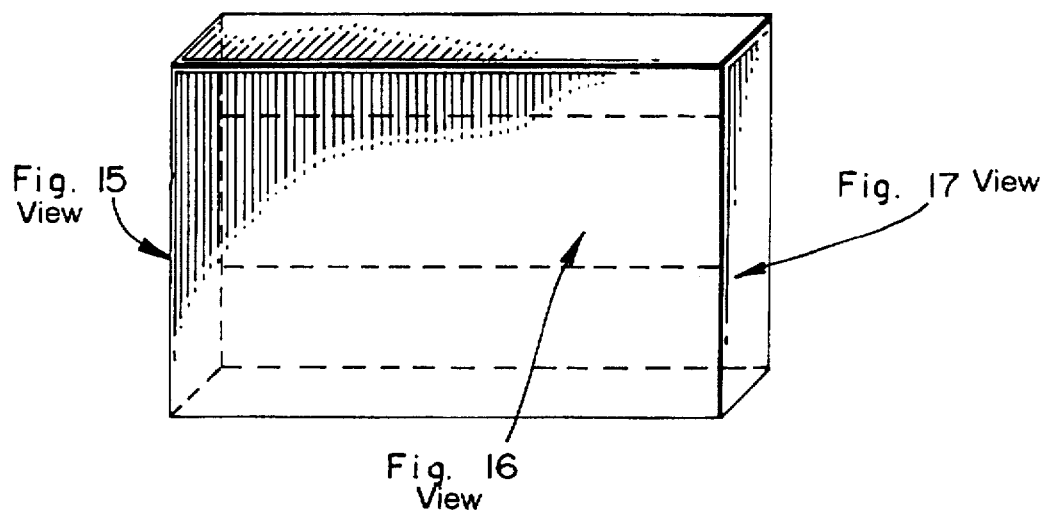
Figure 11:
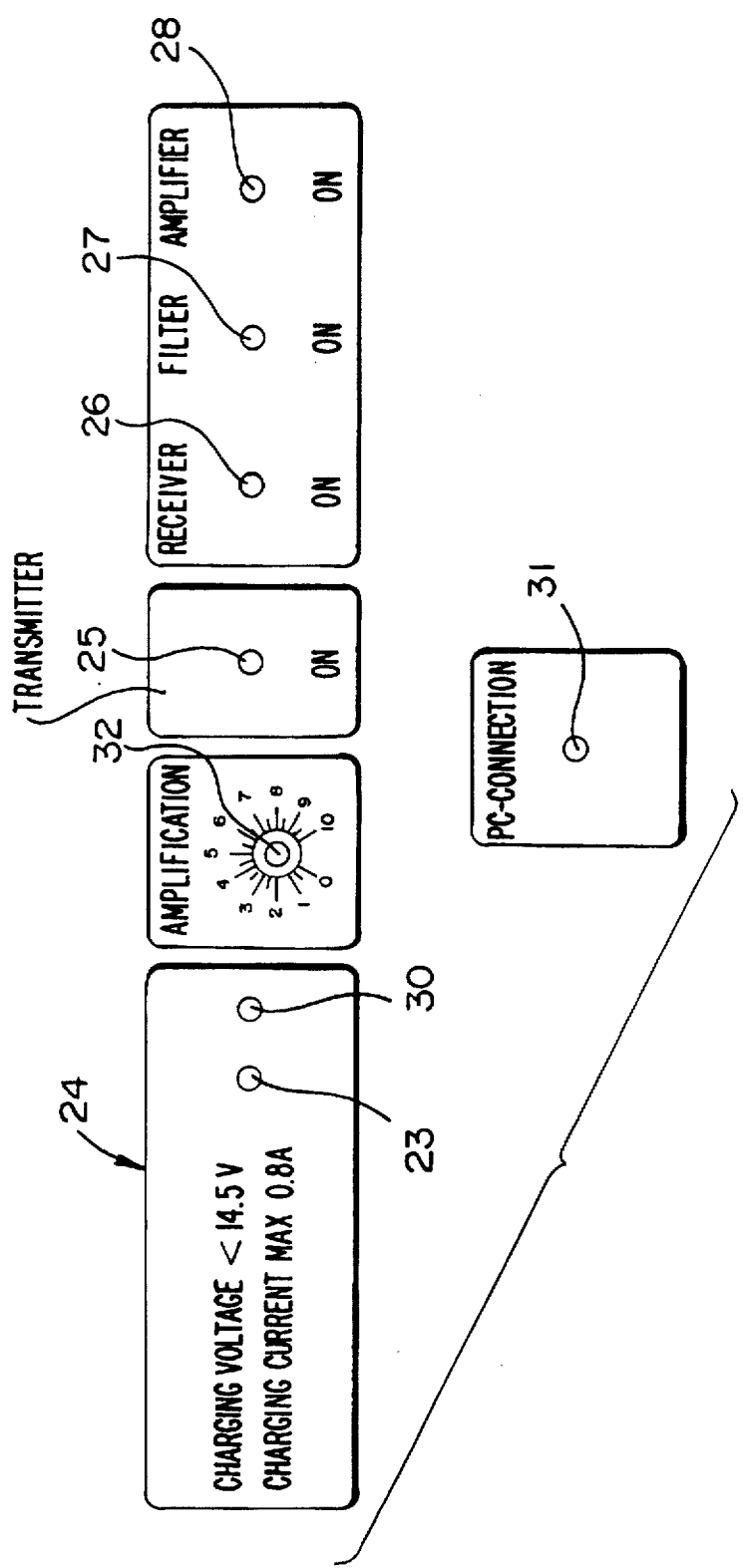
Figure 12:
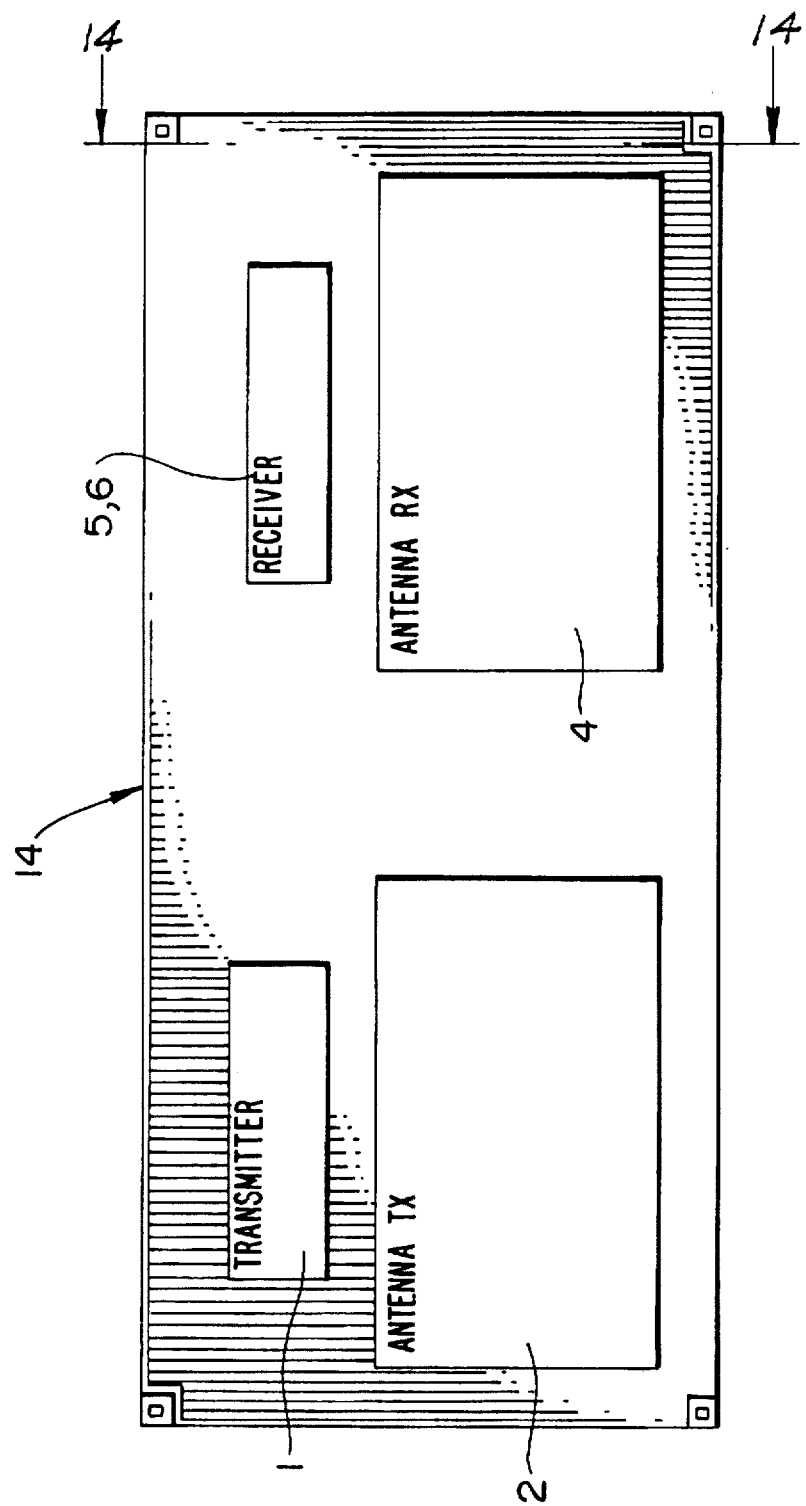
Figure 13:
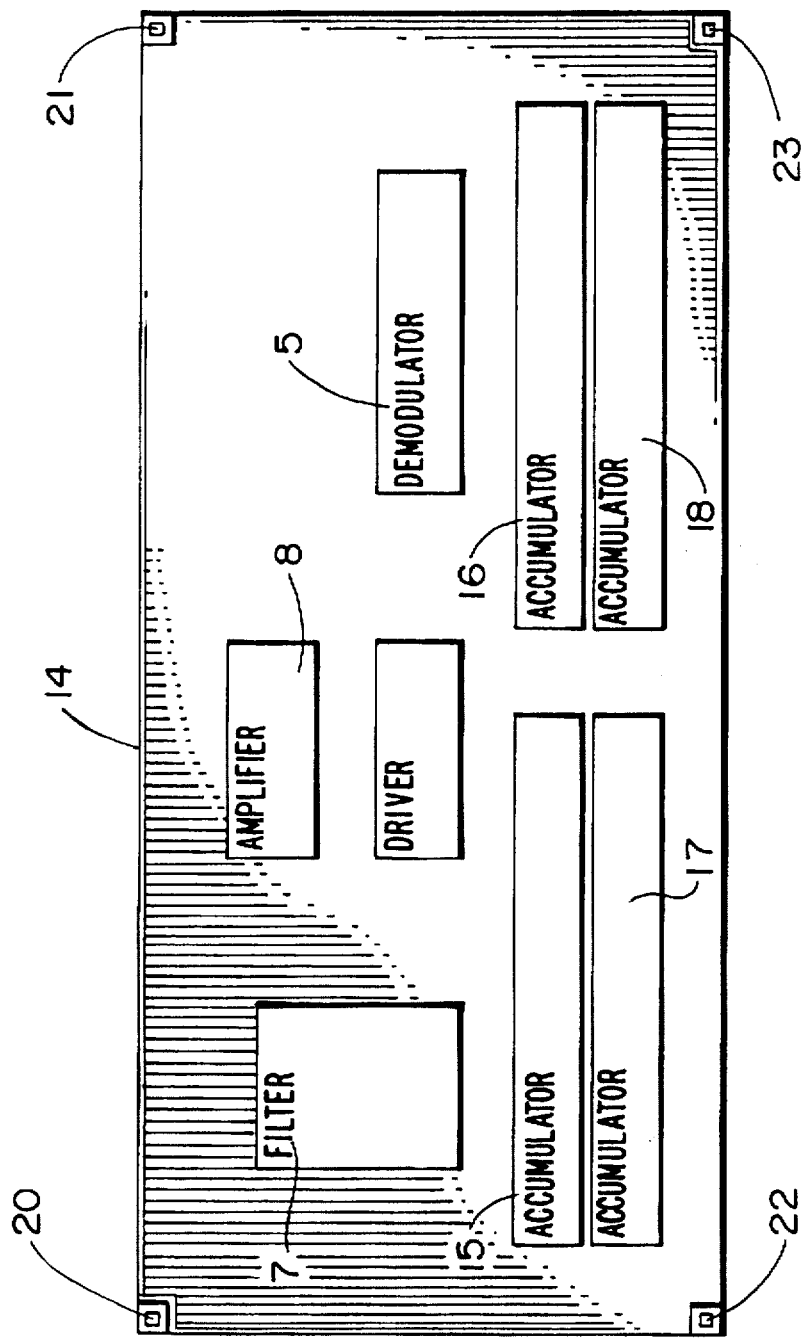
Figure 14:
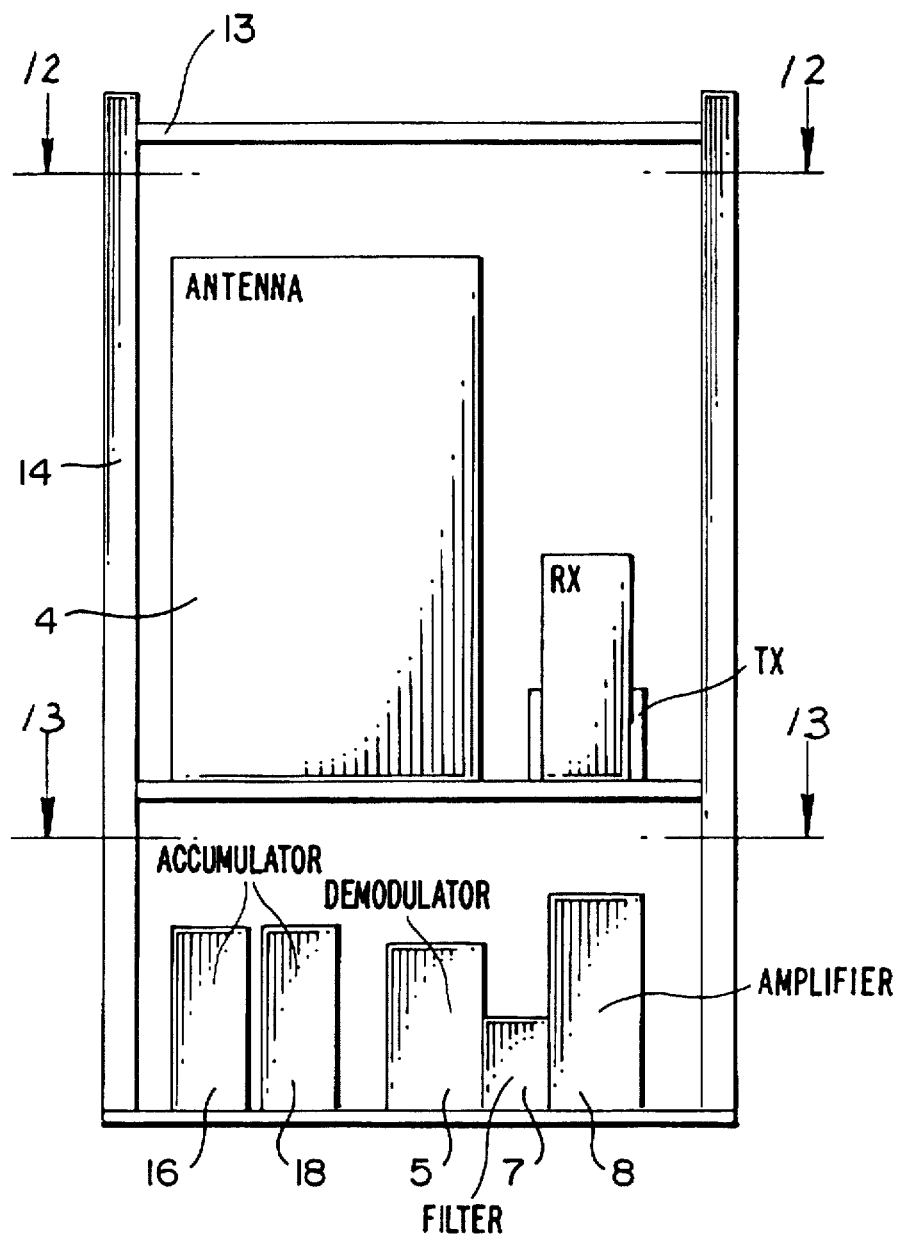
Figure 15:
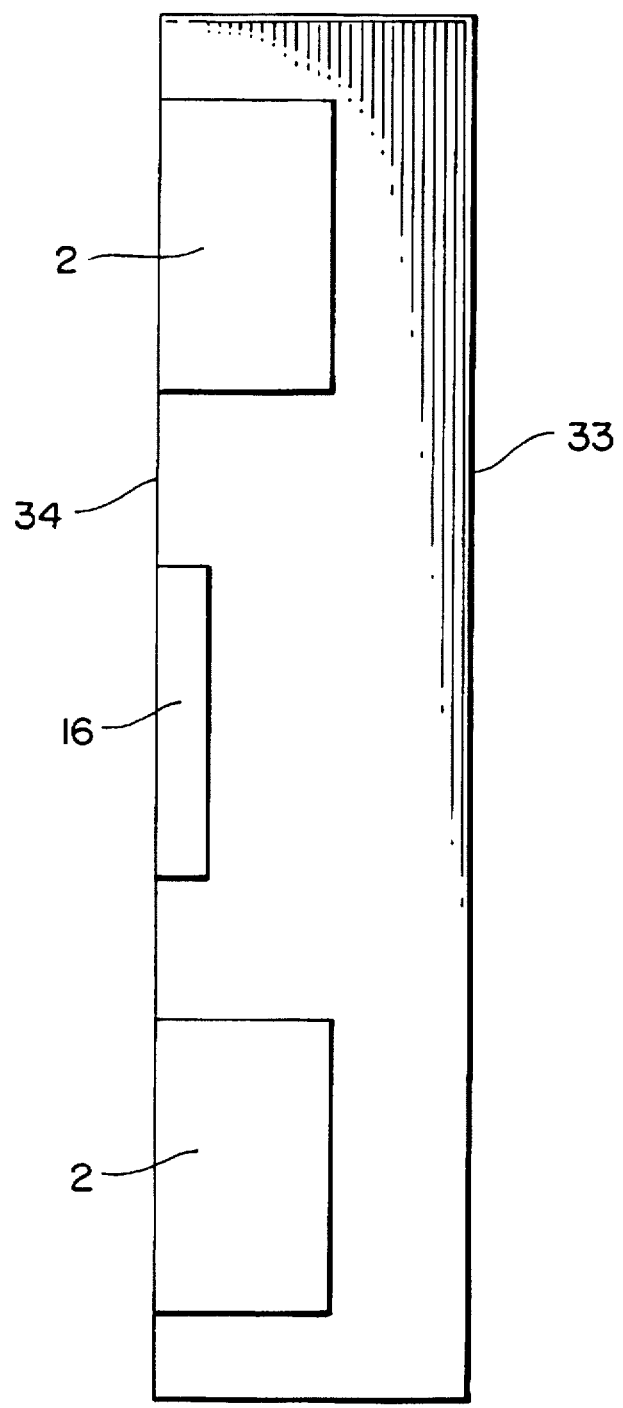
Figure 16:
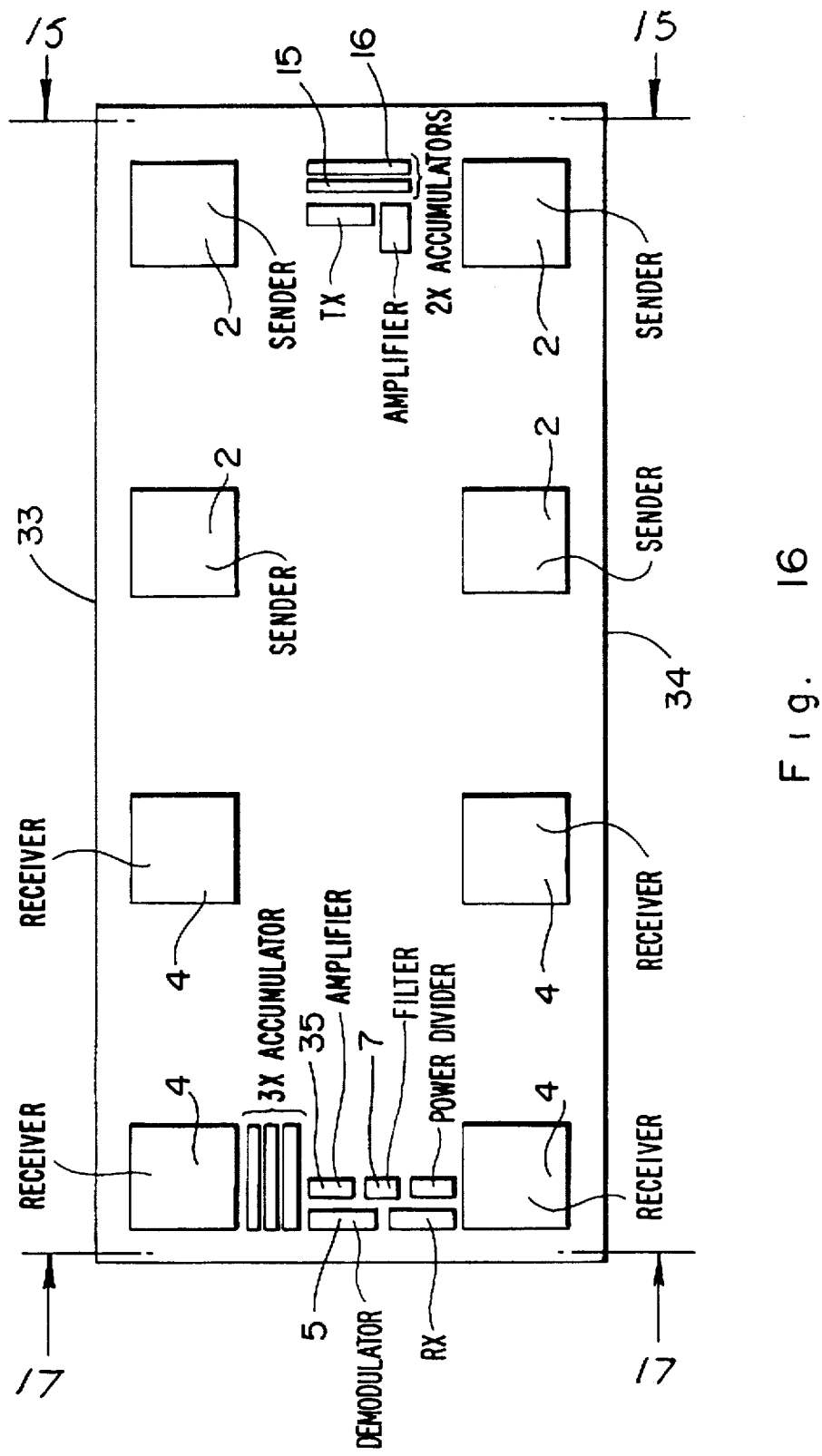
Figure 17:
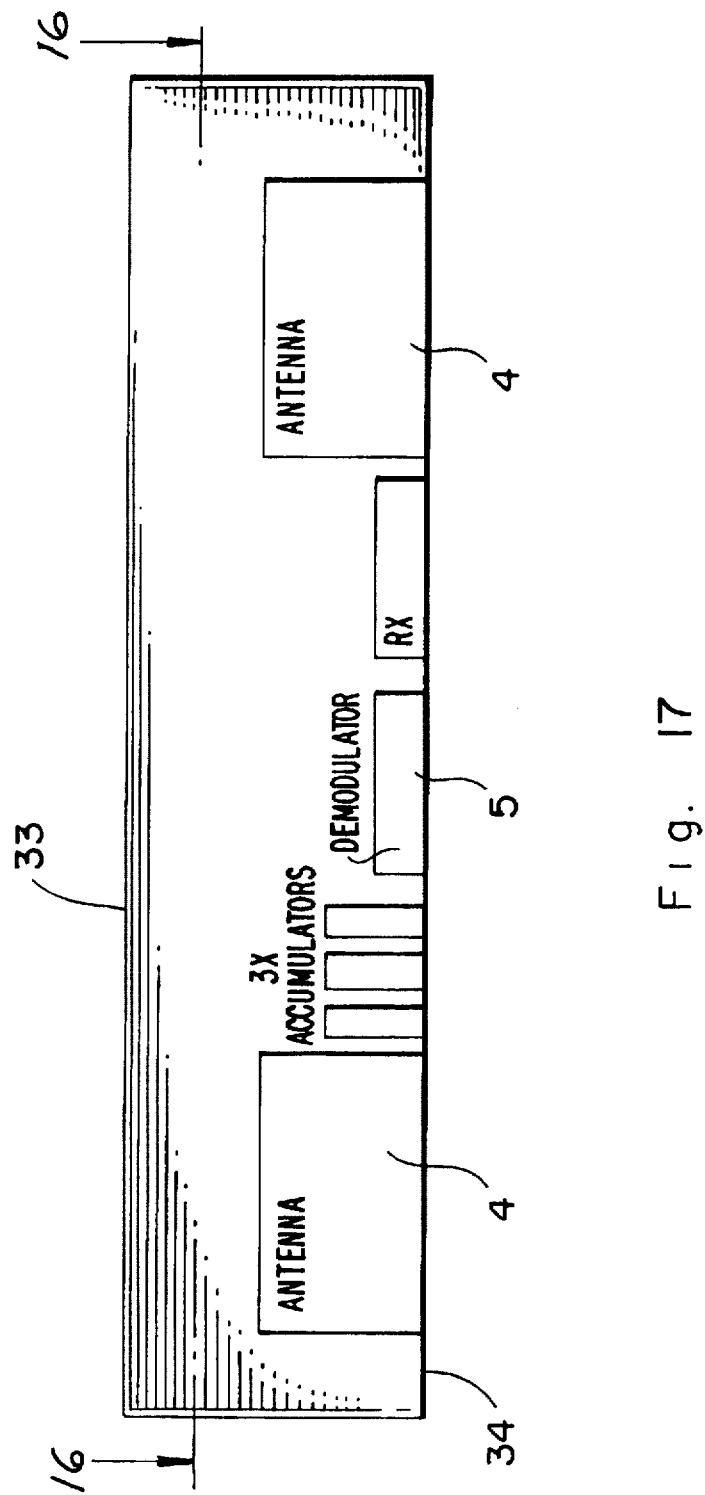

The invention is described in detail hereinafter by means of embodiments given by way of example with reference to the accompanying drawings in which:

FIG. 1 is a diagrammatic view of the main units of an embodiment of the apparatus according to the invention, FIG. 2 is a diagrammatic view of a simpler embodiment of the apparatus according to the invention with the main components thereof, FIG. 3 is a diagrammatic view of the structure of the evaluation chain, FIGS. 4 and 4a show a flow chart of the implemented processing steps, FIGS. 5 and 6 are spectral representations of electromagnetic signals detected with the apparatus according to the invention, with frequency components which are characteristic of living bodies, FIG. 7 shows a diode direct receiver without converter connected upstream thereof, FIG. 8a shows a circuit diagram of an analog high pass filter and an anti-aliasing filter in the form of a low pass filter, FIG. 8b shows a circuit diagram of voltage symmetrising, FIG. 9 is an overview illustration relating to FIGS. 11 through 14, illustrating a second transportable embodiment according to the invention, FIG. 10 is an overview representation relating to FIGS. 15 through 17, illustrating a third embodiment according to the invention which is arranged stationarily in a rectangular tank or case, FIG. 11 shows an operating panel of the second embodiment according to the invention, from above, FIG. 12 is a sectional view taken along line A—A in FIG. 14, FIG. 13 is a sectional view taken along line B—B in FIG. 14, FIG. 14 is a sectional view taken along line C—C in FIG. 12, FIG. 15 is a sectional view of the third embodiment according to the invention along line F—F in FIG. 16, FIG. 16 is a sectional view of the third embodiment according to the invention along line D—D in FIG. 17, and FIG. 17 is a sectional view of the third embodiment according to the invention along line E—E in FIG. 16.

The invention is firstly described hereinafter more generally and then in greater detail with reference to individual embodiments.

FIG. 1 shows an arrangement with a transmitter 1 and a transmission antenna 2 which transmit at a fixed frequency which is preferably in the range of some 100 MHz through about 10 GHz.

The transmission antenna 2 preferably has a lobe-shaped fixed directional characteristic. Depending on the respective embodiment of the invention the transmitter 1 and the antenna 2 are in the form of a portable unit or are mounted stationarily. The receiver device which is generally identified by reference 3 and which is shown in a simpler embodiment in FIG. 2 includes a receiving antenna 4 connected to a direct demodulator 5 which, from the received electromagnetic signal, demodulates the frequency components which are characteristic of living bodies. That demodulation effect is performed in the form of phase or frequency demodulation and can already provide the desired frequency components at the output of the direct demodulator 5.

In comparison with the embodiment of the direct demodulator shown in FIG. 7, it may also comprise a rectifier bridge of known kind which results in a voltage-doubled or voltage-multiplied useful signal.

In a further configuration, the receiving device 3 includes a frequency conversion device 6 which is connected upstream of the demodulator 5 and which as a converter converts signals received above about 200 megahertz to terahertz into frequency ranges in which the direct demodulator 5 has increased reception powers. When using diodes, a bipolar or a field effect transistor, that suitable, downwardly converted optimum working range is at about 100 kHz through 200 MHz.

Connected downstream of the direct demodulator is a filter device 7 for filtering out undesired signal components, which limits the band width of the electromagnetic signal, prior to the sampling operation (prior to the analog/digital conversion operation), towards high frequencies. That filter device 7 also limits the band width towards low frequencies. The amplifier 8 connected downstream of the filter 7 increases the voltage or in an alternative configuration the current of the received signals and passes it for sampling to an analog/digital converter 9.

After analog/digital conversion the frequency components which are characteristic of living bodies are processed by a computer device 10 for spectral analysis and spectrally represented. In that case the intensity of the frequency components which are characteristic of living bodies gives information about the presence of the vital functions of the human bodies detected.

In the event of evaluation of the signals in respect of time, the digital signal, for removing distortion thereof, is folded or convoluted with the inverse transfer function of the receiving device 3.

As reliable detection of those signal is extremely difficult, the direct receiver with the non-linear element will be described hereinafter, on the basis of a diode direct receiver.
Diode direct receiver The reflected signal is phase or frequency modulated. Detection of that modulation is not possible, or is possible only with extreme difficulties, with the usual reception procedures for FM (frequency modulation) and PM (phase modulation). So that a signal which is phase modulated with 0.2 Hz can be detected, for example with 10 GHz, accurately to 0.2±0.02 Hz, short term-stable synchronised oscillators with deviations of less than $10^{-12}$ would be necessary. That seemed hitherto unattainable from a technical point of view.

A way of directly detecting the modulation of the received signal was therefore sought.

Suitable for that purpose are for example components with very substantially quadratic characteristics; they are inter alia field effect transistors, components with exponential characteristics which in a portion-wise manner can be approximated as quadratic, diodes and transistors. If now the sum of two frequencies is applied as the impressed, received voltage, that results in higher-order terms.

If there is a quadratic term, difference frequencies also occur, beside the rectified current. In order to demodulate the phase-modulated signal which is reflected by the person to be detected, a conventional rectifier can thus already surprisingly be used, in spite of the very high requirements in regard to frequency behaviour.

The phase-modulated signal is impressed on the non-linear characteristic, and that results in currents which are proportional to the phase modulation frequency $\Omega$ and the multiples thereof $k*\Omega$. The curve shape of the modulation is not retained, in consideration of the demodulation principle, but it has been found that those changes in the curve shape are not critical for most uses according to the invention as detection of the modulation can be sufficient for such uses.

The signal-noise ratio determines the sensitivity limit, in the case of direct detection. For the respiration rate, SN values of over 46 dB were achieved, while for the heart rate values of 26 dB were achieved at a distance of 3 mm and with oscillator powers of about 5 mw.

On the assumption that the heart emits spherical waves, between the transmission and reception powers, there is a relationship which is inversely proportional to the second power of the distance. Therefore, for the ratio of the amplitudes of the respiration rate UA to the noise UN or the heart rate UH to the noise, it is possible to estimate that the reception limit with a transmission power of 1 W is then at about 50 m in relation to the heartbeat and at typically 160 m in relation to respiration.

Antennae with a higher gain and low-noise components can correspondingly increase those values in accordance with the invention. That means that sufficient reception signals are still to be expected in the location operation, even for ground layers of several metres thickness.

The diode which is ideal in terms of saturation current IO and temperature voltage is the Si power diode 1N4004 whose suitability as a rectifier is however limited to high frequencies due to the high barrier layer capacitance. After that follows the low-signal Si diode 1N4148, then the Si Schottky diode BAT 46 and finally the two Ge diodes AA116 and AA144.

A diode direct receiver was respectively adjusted for 440 MHz, 1.3 GHz, 2.4 GHz, 5.6 GHz and 10 GHz. For 4 of the 5 frequencies, receiving antennae were designed with a direct diode receiver:

440 MHz: half-wave dipole with v=0.940, Z=60.5Ω and BAT 46

1.3 GHz: half-wave dipole with v=0.906, Z=57.4Ω and BAT 46

2.4 GHz: half-wave dipole with v=9.40, Z=60.5Ω and BAT 46

5.6 GHz: full-wave multi-wire triadic dipole with v=0.73, Z=140Ω and BAT 46.

It was already found with that receiver that the level of sensitivity fell greatly, relative to the 2.4 GHz receiver. At 10 GHz, it was no longer possible to detect a usable voltage so that the construction of a 10 GHz diode direct receiver was abandoned. The available diodes no longer exhibited any usable rectifier effect at high frequencies of that kind.

As signals according to the invention can be graded by experts as being below the measurement limit, great attention has been paid to the types of antenna used.

Antennae

The front-back ratio must be made as large as possible, for the location procedure, in order not to receive signals which are incident in opposite relationship to the main emission direction. Secondary lobes must also be minimised for that reason. Therefore the entire radiation diagram should have a main lobe which is as narrow as possible and no secondary lobes.

The input impedance of the antennae can and should be adapted in accordance with the invention to real or complex impedances in such a way that power adaptation is achieved in the case of transmitters and noise adaptation is achieved in the case of receivers. The fulfillment of those requirements by an antenna design is however not possible at the same time.

All antennae used are endfire antennae as backfire antennae of comparable dimensions always have a worse front-back ratio as the waveguide structure must be excited in the rearward direction. The antennae should be as wide-band as possible as an adjusting operation should not be involved. Logarithmically periodic structures are known as wide-band antennae with a very good front-back ratio. A wide-band nature on the one hand and a pronounced directional effect on the other hand are achieved by virtue of the logarithmic gradation of the waveguide structures. The fact that the gain, compared to resonant antennae of comparable dimensions, is lower, is generally not a problem for the situation of use according to the invention.

The polycone antenna can replace the rotational paraboloid antenna as deviations from the paraboloid configuration which are less than a tenth of a wavelength do not have an adverse effect on the performance of the antenna. Even at a fifth of the wavelength, the loss of amplification is below 2 dB and can thus be disregarded for most cases.

The design configuration of the paraboloid reflector, which is technically difficult to achieve, can thus be replaced by the polycone reflector which is easier to produce, without suffering disadvantages. The feed is however comparably expensive and complicated and the front-back ratio is only improved with reflectors which are large relative to the wavelength and whose illumination is limited to the inner region.

In order to overcome the problems involved in polarisation, in our embodiments with the two higher frequencies (5.6 GHz and 10.368 GHz) a circularly polarised antenna was used in each case, on the one hand as the receiving antenna and on the other hand as the transmitting antenna. Although admittedly that certainly gave rise to losses of typically 3 dB, they however are small in comparison with the losses which can occur in the case of mutually rotated, linearly polarised antennae.

In one embodiment with only one common transmitting/receiving antenna, the incoming and outgoing waves could be successfully separated, by means of a circulator.

Particular attention is also paid to the high-frequency units, in consideration of the difficult conditions to be overcome in terms of measurement procedure.

High-frequency units

The high-frequency units required are set forth hereinafter. The arrangement takes account of the possible links which occur between the modules and the peripheral elements. They correspond to the configurations according to the invention which we designed.

The direct modulators are used at the higher frequencies, that is to say at frequencies above about 200 MHz, after the converters which convert to the intermediate frequency of 137.5 MHz. Both the diodes used and also the transistors are operational at that frequency.

1. Diode mixer

The diode mixer comprises a symmetrical voltage multiplication circuit with a resonance circuit at the input and a low pass filter at the output.

Here, in contrast to the voltage which can be achieved when using a diode as the direct receiver, it is possible to achieve the quadruple output voltage as the sources are now connected in series. The increased internal resistance which is caused thereby is immaterial in terms of function.

In practical operation it was found that the diode mixer is superior, in regard to the signal-noise ratio, to the other known mixer designs.

Low-frequency units

All modules which are operated in the low-frequency range are equipped with their own power supply. That purpose is served by using individual lead accumulators of 12 V/2Ah which are provided with a voltage monitoring circuit and an on switch. Strict separation of all power supply units was found to be necessary as the use of a mains unit already resulted in considerable interference and trouble.

The entire arrangement is thus completely insulated on the transmitter side and on the receiver side it is only connected to the mains by way of the personal computer which however is in the form of a battery-powered unit in the case of portable apparatuses.

1. Pre-amplifier

The pre-amplifier uses a low-noise quadruple operational amplifier. One of the amplifiers is connected as an operating voltage symmetrising means; the other three are connected as band pass filters and are coupled together by way of high pass filters.

A low pass filter limits the noise of the first stage. By means of an optional resistor; it was possible for the diode direct receiver to be supplied with a preconduction current from the pre-amplifier. Overall two pre-amplifier modules with different levels of gain were used. As the sensitivity of the entire arrangement can result in overdriving of the A/D converter and thus a data loss, a regulated amplifier is necessary.

2. Sampling filter (anti-aliasing filter)

Sampling of time-dependent signals must be effected at a frequency which is greater than twice as high as the highest frequency contained in the input signal. Therefore the input signal must be spectrally limited prior to the analog-digital conversion step. Astonishingly, for the purposes of the present invention, that limitation operation must be effected by an analog filter and cannot be replaced by digital processing. If that is not taken into consideration, the situation involves sub-sampling of the spectral components which are above half the sampling frequency. They are mixed into the lower frequency range and irreversibly falsify the signal and therefore the success according to the invention cannot be achieved.

So-called digital anti-aliasing filters which lead the user to believe that band limitation can be effected after the A/D converter are surprisingly found to be completely ineffective in regard to the problem involved; all errors linked to sub-sampling occurred. Subsequent digital correction was no longer possible because of the destroyed signal content.

In general it is to be noted that among men skilled in the art, in regard to analog and digital parameters, there are false ideas such that the design of a measurement system for digital processing of analog parameters on the basis of the specifications of manufacturers and the exclusive use of the hardware and software offered thereby could not achieve the aim involved.

The requirements which are made in respect of the analog anti-aliasing low-pass filter are very high, depending on the respective further processing involved. Thus the dynamic range must be at least 1 bit better than that of the subsequent A/D converter and likewise linear and non-linear distortion effects must be at least 1 bit better than the A/D converter. Although the dynamic range of an N-bit A/D converter in practice is mostly only N-2 bits, those relationships must be borne in mind. The use of switch capacitor filters is possible if the sampling theorem is also taken into consideration in that respect and the dynamic range achieved is sufficient.

Folding or convolution of the input signal with the sampling filter results in amplitude and phase distortions and envelope curve distortions, on the basis of the group transit or delay time of the filters Those signal changes can be taken into consideration if required by a procedure whereby the inverse transfer function of the sampling filter is folded or convoluted with the sampled signal in the computer. That procedure is possible only if sampling was effected correctly. In contrast in the event of sub-sampling the error is further increased.

Between the upper signal frequency fs, the sampling frequency fa, the asymptotic steepness or order of the sampling filter N and the over-sampling factor k, there is the following relationship, in relation to the achievable degree of accuracy or resolution A in bits:

$$k = \frac{\ln(fa) - \ln(fs)}{\ln(2)} - 1$$
$$A = k*N + 1$$

For a limit frequency of fs=2 Hz with a degree of resolution of A=13 bits, that gives for example the following possible configurations:

First-order filter (N=1)→sampling frequency fa=16384 Hz

Third-order filter (N=3)→sampling frequency fa=64 Hz

Sixth-order filter (N=6)→sampling frequency fa=16 Hz.

The last combination is the arrangement used in our embodiments. In the case of low-order filters with 'good-natured' performance in respect of the transfer function, we must surprisingly reckon on extreme over-sampling rates in order to attain usable results. In spite of the high sampling frequency of over 16 kHz, only the spectral components up to 2 Hz are correctly sampled (at A=16 bits, fs=20 kHz and fa=44 kHz filters of the 109th order would be necessary in order to effect sampling in accordance with the sampling theorem).

Over-sampling has a further advantage: even if each analogdigital converter is ideal in respect of its characteristic, it adds the quantisation noise to the signal to be sampled so that the signal is falsified not only by the quantisation operation, that is to say discretisation of the amplitude values, but it is also additionally caused to have noise.

The noise can approximately be considered as white so that, with a larger sampling band width, that is to say with over-sampling, correspondingly less noise falls into the signal band width and thus the signal-noise ratio of the converter but not the signal can be proportionally improved.

The 6th-order sampling low pass filter used is provided by the series connection of two third-order low pass filters (asymptotic edge steepness 18 dB/octave or 60 dB per decade). Each low pass filter comprises an operational amplifier connected as a voltage follower, and an R-C-circuit.

The amplitude, phase and envelope curve distortions due to the frequency and phase characteristics of all filters as well as the group delay or transit times can be reversed by a procedure whereby the time function is folded or convoluted with its inverse transfer function T−1 (w) of the preceding signal path T(w) and thus complete pole-zero location compensation is effected. That can be necessary if the original time signal is to be reconstructed and therefore deformation of the time signal by the converters and the elements of the transmission chain must be avoided. In a situation of use in which the significant detection of a spectral line is required, it is possible to disregard that.

In the structure according to the invention, in one embodiment, the time signal passes from the converter (receiving antenna) to the personal computer (A/D converter) through at least one fifteenth-order high pass filter and a twenty first-order low pass filter which arise out of the product of the transfer functions of the individual elements of the measurement chain (direct mixer, pre-amplifier, 2*low-pass filter, 2* high-pass filter, A/D converter).

If necessary the dynamic behaviour of the analog part of the electronic system can also be improved by units which directly effect pole-zero location compensation. By virtue thereof, it is possible to reduce noise, an unfavourable transmission characteristic can be improved, or optimum transmission properties can be achieved, in accordance with given criteria.

3. High-pass filter

In accordance with the invention spectral limitation of the input signal, with respect to the low frequencies, is desirable for three reasons:

1. 1/f-noise

The amplitude of the 1/f noise increases reciprocally relative to frequency. Therefore, with an increasing measurement time, noise components occur at a lower and lower frequency and falsify the signal to be measured. The main sources for the 1/f noise are the transmission oscillator, the converter oscillator and the operational amplifiers.

2. Slow movements

At a constant speed movements of the body to be detected result in a Doppler frequency shift and thus spectral components which can fall into the frequency band to be investigated. A wide additional band occurs, in the event of irregular movements. The slower the movements, the lower the frequency of the spectra which are then more and more difficult to separate from noise components.

3. Evaluation time

In order to identify a spectral line of the frequency f, measurement must be effected at least for a time t=1/f, that is to say, the lower the frequencies to be detected, the longer the period for which measurements must be made. As it is not possible to guarantee that the measurement time is an integral multiple of the spectral component which is of interest, a leakage effect occurs in the Fourier analysis. That results in spectral spreading. Therefore, when analysing low frequencies, it is necessary to observe a measurement time which is a multiple of the period duration, in which case the degree of accuracy increases proportionally with the measurement time. With 10% errors in the spectral resolution and 0.2 Hz lower frequency it is necessary to reckon on a measurement time of typically 50 seconds.

FIG. 3 shows the general structure of the evaluation chain. Personal computers from the office sector, IBM-PC-compatible type, are used as central units, as the power thereof is adequate for the task involved.

The plan shown in FIGS. 4 and 4a gives an overview of the implemented processing steps, therein F { } denotes the Fourier transformation and F−1 { } denotes the inverse Fourier transformation. Results After various preliminary tests a sampling rate of 16 Hz with a unipolar resolution of 13 bits (total resolution 14 bits)

was found to be well suited. The window width selected for spectral analysis was 512 values, corresponding to about 33 seconds: the Hamming window was selected as the window.

FIG. 5 shows the heart rate of a test person with respiration stopped. The spectral component stands out so clearly from the surroundings that further processing is not necessary to detect the heartbeat of the test person. The quantitative spectrum is plotted in any units, in relation to frequency in Hertz. Measurement was effected at 2.4 GHz, the diode direct receiver, that is to say the ½-dipole, was used as the receiver, the local oscillator was used as the transmitter, respiration was stopped.

FIG. 6 shows the spectrum of the signal reflected by a breathing person, using the diode direct receiver and the logarithmic-periodic Yagi antenna and the 1.3 GHz transmitting oscillator as the source. Both heart rate and also respiration rate are present.

At the frequency of 440 MHz, the tests were found to be difficult, because of the extreme sensitivity of the entire arrangement. Almost all test recordings exhibited overdriving phenomena and reactions to external events.

The problem of overdriving can be resolved by suitable attenuation; detection of respiration and cardiac activity is not influenced thereby.

If a circulator is used, then, as described, it is possible just to use an antenna which transmits and receives simultaneously.

The examples clearly demonstrate that the detection of living people is possible. In that respect neither walls nor distances of some 10 metres are an obstacle worth mentioning. Working frequencies of 1.3 GHz and 2.4 GHz were found to be highly suitable. When using antennae which are still manageable, the level of sensitivity is sufficiently high to achieve reproducible results with clear identification of the heartbeat and respiration without intensive numerical processing steps being necessary, as suitably strong reception signals are already present.

Circuit diagram high-pass and anti-aliasing low-pass filters

The circuit diagram of the unit employed for band restriction is shown in FIGS. 8a and 8b. The third-order high pass filter suppresses the low-frequency noise components, in particular the 1/f noise. The following third-order low-pass filter limits the spectrum to higher frequencies. There then follows a linear amplifier stage for level matching. The operating voltage is electronically symmetrised so that a unipolar supply is sufficient. Two of those units in cascade relationship fulfill the requirements set by the sampling theorem.

Diode demodulator circuit diagram

A diode detector whose circuitry is shown in FIG. 7 serves for phase demodulation of the reception signal which is mixed on to the intermediate frequency and as the direct demodulator for the developed receiver antennae. The circuitry corresponds to a typical power metr ; a preconduction or input current can be impressed from the output. The input impedance can be adapted to the IF-mixer or the antennae.

Diode direct receiver circuit diagram

The diode direct receivers comprise diode detectors which are ½ or 1 wavelength long and which are multiplied by the corresponding shortening factor and are suitably connected upstream. A pre-conduction or input current can be impressed at the output.

In addition each unit is provided with its own stabilised voltage supply and its own on-off switch so that units with a long time constant (local oscillators, pre-amplifiers, low-pass filter) could be operated in continuous duty and were in thermal and electrical equilibrium while consumers or loads with a high current consumption (final transmitting stages, converters) can be switched off between uses.

Preferred specific embodiments

In a first preferred embodiment the apparatus according to the invention includes a polycone antenna which is not specifically illustrated in the Figures and which portion-wise simulates a shallow parabolic antenna, as the transmitting/receiving antenna 2,4. The transmitting/receiving antenna 2,4 is provided with a circulator which effects decoupling between the transmitted and the received signals.

An operation of definedly searching target detection areas can be effected with a mechanical tilt inclining device and scales preferably associated with pivot angles. In that respect, motor-driven tracking of the inclining device about its pivot axes with electronic control for rastor-like covering of the target detection area permits automated recording of data, even in areas which are inaccessible to human beings, such as for example in areas with nuclear contamination, areas which are endangered by earthquakes or areas which are threatened by chemical explosions. In addition a threshold value function in the above-identified frequency range can define values, above which signalling of the detection of a living person is effected.

In a second version according to the invention all electronic units up to the analog/digital converter 9 are disposed in a pilot suitcase. The suitcase version represents a complete system for detecting living persons or living creatures.

Disposed in a pilot suitcase 14 are two shortened antennae 2, 4 with angled reflectors and folded dipole exciters. The antenna Tx used as the transmitting antenna 2 is connected to a transmitter which, at a working frequency of 1300.0 MHz, at a substitute or equivalent load of real 50 Ω, outputs a power of 6 mW. The horizontal aperture angle of each antenna is 54° while the vertical angle is in each case 64°. The gain, ascertained by comparison with a calibrated reference antenna, is 6.7 dBi in each case. The receiving antenna 4, Rxis connected to a receiver which, by means of the converter 6, converts the incoming signals into the frequency range around 137.5 MHz. That is then followed by the demodulator 5, the amplifier 8, the filter 7 and a driver. Four rechargeable lead-gel accumulators 15, 16, 17, 18 serve as the power supply. The units are arranged in a frame 19 of aluminium members 20, 21, 22, 23 in two planes. The upper third plane is formed by the front plate 24 with the operating elements. For service purposes the entire insert can be completely removed from the suitcase 14.

The front plate 24 carries four on-off switches 25, 26, 27, 28 which are associated with the respective components, two 4 mm charging sockets 29, 30, a multi-pole socket 31 for data transmission to the PC and a manually actuable level setter 32 for reducing the signal amplitude of the output signal. A PC with incorporated analog-digital converter is connected by way of a flexible connection. Evaluation of the measured signals is effected by a software program which is adapted for this use and which performs the method steps shown in FIGS. 4 and 4a.

From the transmitter an unmodulated signal is emitted by way of the transmission antenna 2, Tx. If the signal encounters a living creature, then respiration and heartbeat cause phase modulation of the waves reflected at the corresponding surfaces. The reflected waves are received by the receiving antenna Rx, converted by the receiver to a lower intermediate frequency and phase-demodulated in the demodulator 5.

The information sought is now present in the form of low-frequency voltage fluctuations. They are amplified and restricted by means of filters in the band width to frequencies of between 0.05 Hz and 4 Hz. An anti-aliasing filter 7 prevents the occurrence of aliasing frequencies, caused by sampling of the signal in the analog-digital conversion operation. The screening mesh of the transmission cable is driven to prevent external interference radiation phenomena. The resulting compensation of the cable capacitance permits line lengths of several 100 metres between the personal computer with the analog/digital converter and the suitcase. The software permits the user to select time intervals in respect of the signal. After selection of a window function, transformation from the time region into the frequency region is effected.

Evaluation of the spectrum by the user is supported by statistical evaluation regarding the probability of the presence of a living person, which is based on the previously acquired experience. A further statistical formulation or estimate supplies the range of distances in which the detected person is expected to be.

By virtue of the compact configuration and the aspect of mobility, the following areas of use present themselves for the suitcase version: in the case of police authorities for portable monitoring and surveillance generally, and for monitoring the perpetrator and hostages in a situation involving the taking of hostages, monitoring empty buildings and vehicles, monitoring tunnel and passage constructions, and in combatting terrorism and extremism, on the part of customs and frontier authorities, for example for checking containers for the presence of a living creature, or vehicle checking.

In the third embodiment according to the invention the apparatus is disposed in a stationary and mounted rectangular tank or box. Disposed in a metal tank or box 33 with a plastic bottom 34 which is transmissive of high frequencies are eight shortened antennae 2, 4 with angled reflectors and folded dipole exciters.

Antennae which are connected together in four groups are connected as transmission antennae 2 to an amplifier 35 which, fed by a transmitter 1, Tx, at a working frequency of 1300.0 MHz, at a substitute or equivalent load of real 50 Ω, outputs a power of 600 mW. The horizontal aperture angle of each antenna is 54° while the vertical angle is 64° in each case. The gain is the same as in the suitcase version. The receiving antenna 4 which is also combined out of a group of four antennae is connected to a receiver Rx which converts the incoming signals by means of a converter 6 into the frequency range of 137.5 MHz. That is then followed by the electronic evaluation system already described in connection with the second suitcase version according to the invention.

The third embodiment according to the invention is used in connection with stationary uses. That includes customs and frontier authorities and operators of tunnels and large buildings. Monitoring and surveillance of empty buildings, empty vehicles, monitoring tunnel and passage structures and the use in endangered buildings for combatting terrorism and extremism are also possible. Container checking for the presence of a living creature can be effected in a covert manner so that even blind passengers can be detected at frontier crossings or in railway or aircraft loading areas.

I claim:

1. Apparatus for detecting the presence of living bodies by means of electromagnetic signals and a receiver device for receiving electromagnetic signals, wherein the receiver device (3) for receiving electromagnetic signals includes a device for obtaining frequency components which are characteristic in respect of living bodies, out of the received electromagnetic signals, characterised in that the receiver device (3) includes a direct demodulator that demodulates the received signals to obtain said frequency components, wherein said demodulator includes a component with a non-linear current/voltage characteristic as a frequency-selective element for selecting said frequency components as output.

2. Apparatus as set forth in one of claim 1 characterised in that the receiver device (3) includes a frequency conversion device (6) connected upstream of the demodulator (5).

3. Apparatus as set forth in one of claim 1 characterised in that all electronic units in the signal path upstream of digital evaluation operation, including their voltage supply, are disposed in a transportable suitcase.

4. Apparatus as set forth in claim 1 characterised in that all electronic units in the signal path upstream of digital evaluation operation, including their voltage supply, are arranged in a rectangular, stationarily mounted box.

5. Use of an apparatus as set forth in claim 1 in places of imprisonment and detention for monitoring the condition of inmates.

6. Use of an apparatus as set forth in claim 1 for object monitoring and/or safeguarding including persons therein.

7. Use of an apparatus as set forth in claim 1 for detecting and/or locating living bodies in catastrophe protection, in particular earthquakes, landslides, avalanches, building collapses and/or fires.

8. Apparatus as set forth in claim 1 characterised in that the direct demodulator demodulates the frequency components which are characteristic in respect of living bodies directly out of the received electromagnetic signals.

9. Apparatus as set forth in claim 8 characterised in that the direct demodulator (3) includes a diode, a bipolar or a field effect transistor as the frequency-selective element.

10. Apparatus as set forth in one of claim 1 characterised in that the apparatus includes a transmission device (1) for the transmission of an electromagnetic carrier signal at a fixed frequency.

11. Apparatus as set forth in claim 10 characterised in that the carrier signal is in a frequency range of approximately one MHz to approximately one THz.

12. Apparatus as set forth in one of claim 1 characterised in that the device for obtaining frequency components which are characteristic in respect of living bodies includes a filter device (7), a sampling device, an A/D converter (6) and a computing device (10) for spectral analysis.

13. Apparatus as set forth in claim 12 characterised in that the filter device (7) includes at least one analog sampling filter.

14. Apparatus as set forth in claim 13 characterised in that the sampling filter limits the band width of the demodulator output signal towards high frequencies prior to the sampling operation and prior to the A/D conversion operation.

15. A method of detecting the presence of living bodies by means of the reception of electromagnetic signals, in which frequency components which are characteristic in respect of living bodies are obtained from the received electromagnetic signals, characterised in that the received electromagnetic signals are directly demodulated by a direct demodulator to obtain said frequency components, wherein said demodulator includes a component with a non-linear current/voltage characteristic as a frequency-selective element for selecting said frequency components as output.

16. A method as set forth in claim 15 characterised in that the received electromagnetic signals is converted to an intermediate frequency.

17. A method as set forth in claim 15 characterised in that the received signals are limited in analog manner towards high and low frequencies.

18. Use of a method as set forth in claim 15 in places of imprisonment and detention for monitoring the condition of inmates.

19. Use of a method as set forth in claim 15 for object monitoring and/or safeguarding, including persons therein.

20. Use of a method as claimed in claim 15 for detecting and/or locating living bodies in catastrophe protection, in particular earthquakes, landslides, avalanches, building collapses, and/or fires.

21. A method as set forth in claim 15 characterised in that the received electromagnetic signals are sampled after a filtration operation and converted into a digital signal.

22. A method as set forth in claim 21 characterised in that the digital signal is folded with a window function in the time region and with the inverse transfer function of the receiving device.

23. A method as set forth in claim 21 characterised in that the digital signal is transformed from the time region into the frequency region prior to its evaluation and representation as an output signal.

24. A method as set forth in claim 23 characterised in that the transformed signal is analysed in a frequency range of from about 0.01 Hz through about 10 Hz for the frequency components of cardiac and/or respiration activity, which are characteristic in respect of living bodies.

25. A method as set forth in claim 24, characterised in that the transformed signal is analyzed in a frequency range of about 0.02 Hz through about 3 Hz.

* * * * *